(12) United States Patent
Dzwonkiewicz

(10) Patent No.: US 8,216,132 B2
(45) Date of Patent: Jul. 10, 2012

(54) GEAR-SHAPED LIFTING CAP FOR A LARYNGOSCOPE

(76) Inventor: Mark R. Dzwonkiewicz, Crystal Lake, IL (US)

( * ) Notice: Subject to any disclaimer, the term of this patent is extended or adjusted under 35 U.S.C. 154(b) by 282 days.

(21) Appl. No.: 12/472,568

(22) Filed: May 27, 2009

(65) Prior Publication Data
US 2009/0299145 A1 Dec. 3, 2009

Related U.S. Application Data

(60) Provisional application No. 61/126,705, filed on May 30, 2008.

(51) Int. Cl.
*A61B 1/267* (2006.01)
(52) U.S. Cl. .......................... 600/194; 600/197
(58) Field of Classification Search .......... 606/53, 606/54, 56, 59; 600/185–246
See application file for complete search history.

(56) References Cited

U.S. PATENT DOCUMENTS

| 5,065,738 | A | 11/1991 | Van Dam |
| 5,904,650 | A | 5/1999 | Wells |
| 6,217,514 | B1 | 4/2001 | Gruen et al. |
| 6,355,028 | B2 * | 3/2002 | Castaneda et al. ............ 606/1 |
| 6,454,704 | B1 * | 9/2002 | Dzwonkiewicz ............ 600/185 |

OTHER PUBLICATIONS

Endotracheal Intubation; Reference: Associate Clinical Nurse Manager, High Dependency Unit May 2002 http://dgholgate.tripod.com/endotrachealintubation.html.*
Cricoid pressure. (2006). In Churchill Livingstone's Dictionary of Nursing. Retrieved from: http://www.credoreference.com/entry/ehscldictnursing/cricoid_pressure.*
PHTLS Prehospital Trauma Life Support, Sixth Edition, 2007, pp. 143, 150, 154, 155, Mosby Jems Elsevier, St. Louis, Missouri, US.

* cited by examiner

*Primary Examiner* — Eduardo C Robert
*Assistant Examiner* — Stuart S Bray
(74) *Attorney, Agent, or Firm* — Matthew J. Esserman

(57) ABSTRACT

A lifting cap for attachment to a handle of a laryngoscope for facilitating oral endotrachael intubation. The lifting cap includes an undulating side wall that forms a plurality of finger-grip notches. The finger-grip notches enable a second user to securely grip the lifting cap while a first user grips the handle of the laryngoscope during an intubation procedure.

3 Claims, 7 Drawing Sheets

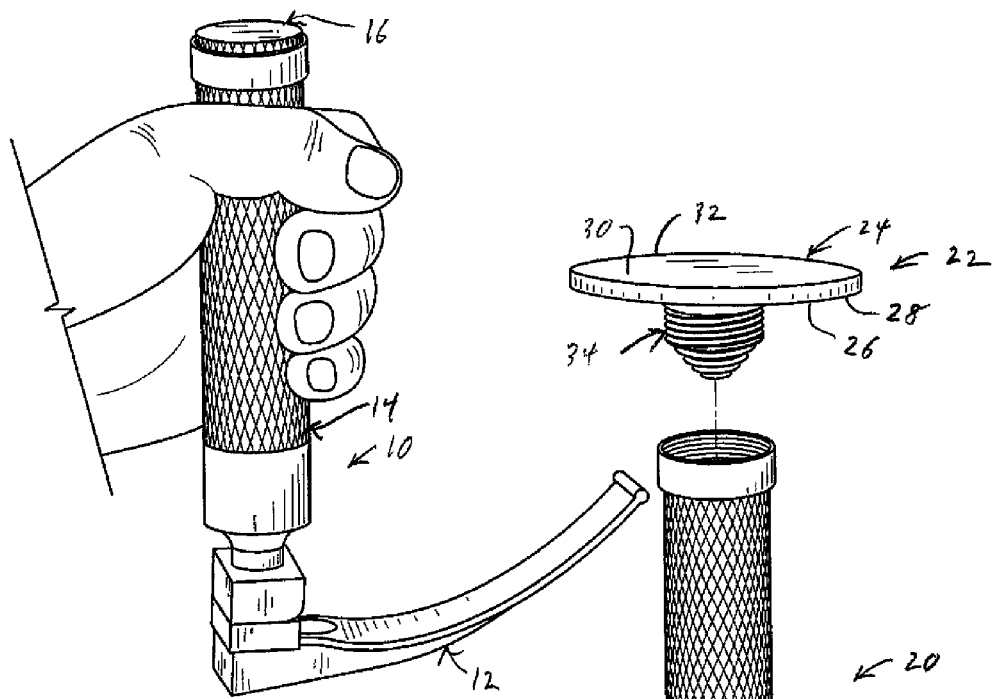
FIG. 1
(Prior Art)
FIG. 3
(Prior Art)
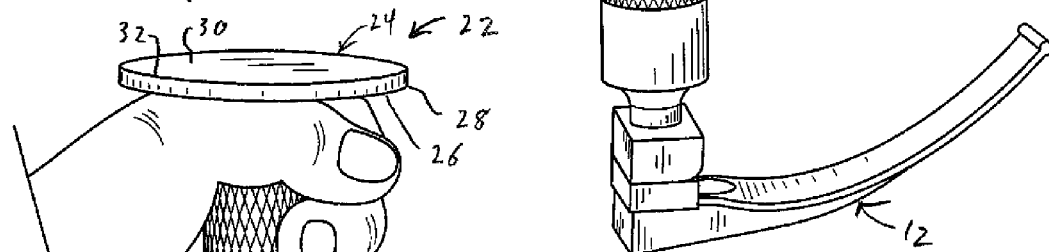
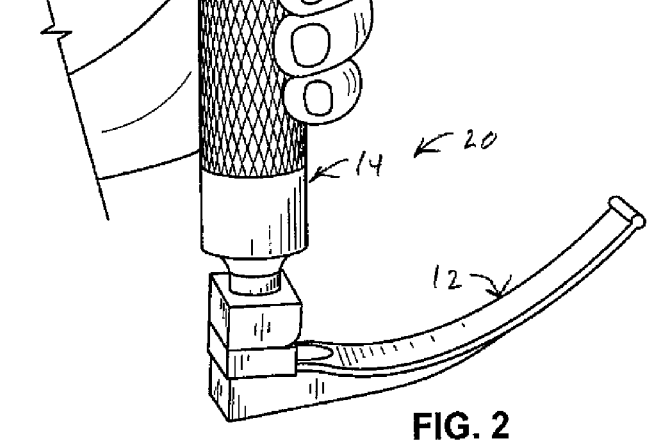
FIG. 2
(Prior Art)

GEAR-SHAPED LIFTING CAP FOR A LARYNGOSCOPE

RELATED APPLICATIONS

This application claims priority to U.S. Provisional Application Ser. No. 61/126,705, filed May 30, 2008, which is expressly incorporated by reference herein.

BACKGROUND

The present invention is directed to a lifting cap adapted to be attached to the distal end of the handle of a laryngoscope to facilitate oral endotracheal intubation of a patient, and in particular to a generally gear-shaped lifting cap including an abutment member having an undulating peripheral side wall that forms a plurality of finger-grip notches such that the handle of the laryngoscope can be gripped by a hand of a first user and the peripheral side wall of the abutment member can be securely gripped by a hand of a second user.

In performing an oral endotracheal intubation procedure the blade of a laryngoscope is inserted into the mouth of a patient. The tip of the blade is positioned at or near the epiglottis depending on whether a straight or curved laryngoscope blade is being used. Previously, a single user manually gripped the handle of the laryngoscope with the left hand of the single user, and the single user lifted the laryngoscope along the central axis of the laryngoscope handle to lift the epiglottis and allow direct viewing of the vocal cords. While the single user gripped the handle of the laryngoscope with the left hand of the single user, the single user inserted an endotracheal tube into the oral opening of the patient and into the larynx of the patient with the right hand of the single user. Excessive force in gripping the handle by the single user often resulted in undesired cranking or rotating of the laryngoscope which can cause trauma to the airway, broken or damaged teeth of the patient, and failed intubation attempts.

SUMMARY

A lifting cap for attachment to an end of a handle of a laryngoscope. The lifting cap comprises an abutment member including a central axis, a proximal surface having an undulating peripheral edge, and a distal surface having an undulating peripheral edge. The distal surface is spaced apart from and overlies the proximal surface. The abutment member also includes an undulating peripheral side wall extending around the central axis in an undulating manner and extending between the peripheral edge of the proximal surface and the peripheral edge of the distal surface. The undulating peripheral side wall forms a plurality of finger-grip notches disposed about the central axis and a plurality of peaks disposed about the central axis. Each finger-grip notch is located between an adjacent pair of peaks. Each finger-grip notch is configured to receive a finger of a user. The lifting cap also includes a fastener attached to the proximal surface of the abutment member. The peripheral edge of the proximal surface is spaced outwardly from the fastener. The fastener is adapted to attach the abutment member to the end of the handle of the laryngoscope.

BRIEF DESCRIPTION OF THE DRAWING FIGURES

FIG. 1 is perspective view showing a prior art laryngoscope being manually grasped with the left hand of a sole user.

FIG. 2 is a perspective view showing a prior art laryngoscope with a lifting cap being manually grasped with the left hand of a sole user.

FIG. 3 is an exploded view of the laryngoscope of FIG. 2.

DETAILED DESCRIPTION

Figure 4:
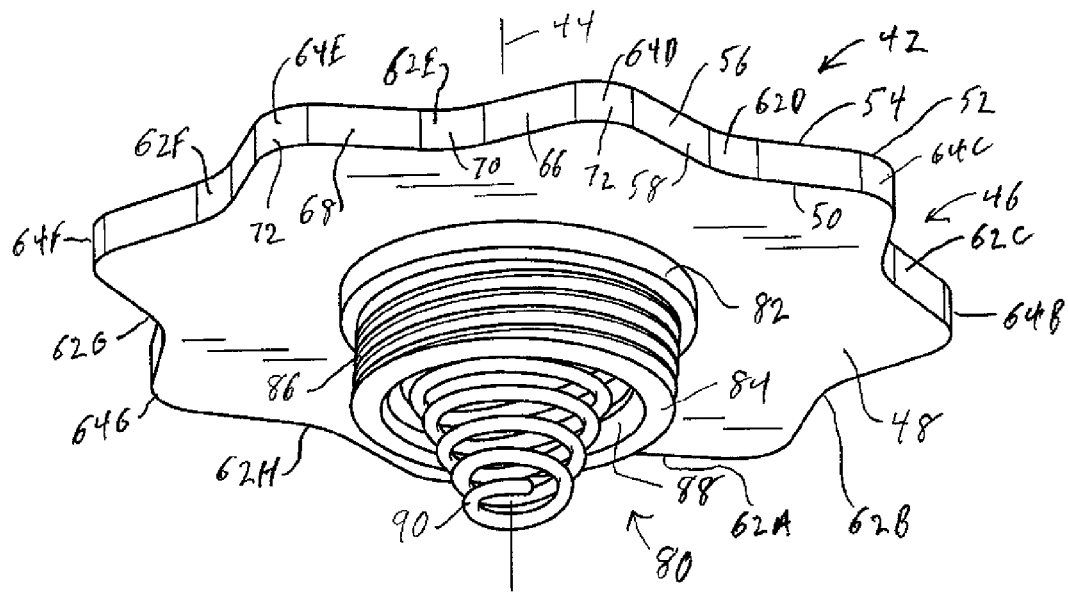
FIG. 4 is a perspective view of the generally gear-shaped lifting cap of the present disclosure configured for use with a laryngoscope.

FIG. 1 shows a prior art laryngoscope 10 being manually grasped by the left hand of a single user. The laryngoscope 10 includes a blade 12 that is attached to a generally cylindrical handle 14. Handle 14 is often tubular such that it may contain one or more batteries. The laryngoscope 10 includes a threaded end cap 16 that is removably attached to an internally threaded distal end of handle 14. End cap 16 has a diameter that is approximately equal to the diameter of handle 14.

A prior art laryngoscope 20 is shown in FIGS. 2 and 3 including blade 12 and handle 14. A lifting cap 22 is removably attached to the distal end of the handle 14. Lifting cap 22 includes a plate 24 having a proximal surface 26 with a circular peripheral edge 28 and a distal surface 30 having a circular peripheral edge 32. Lifting cap 22 includes a fastener such as an end cap 34 that may be formed substantially identical to end cap 16. End cap 34 includes an end wall that is attached to proximal surface 26 of plate 24.

Figure 5:
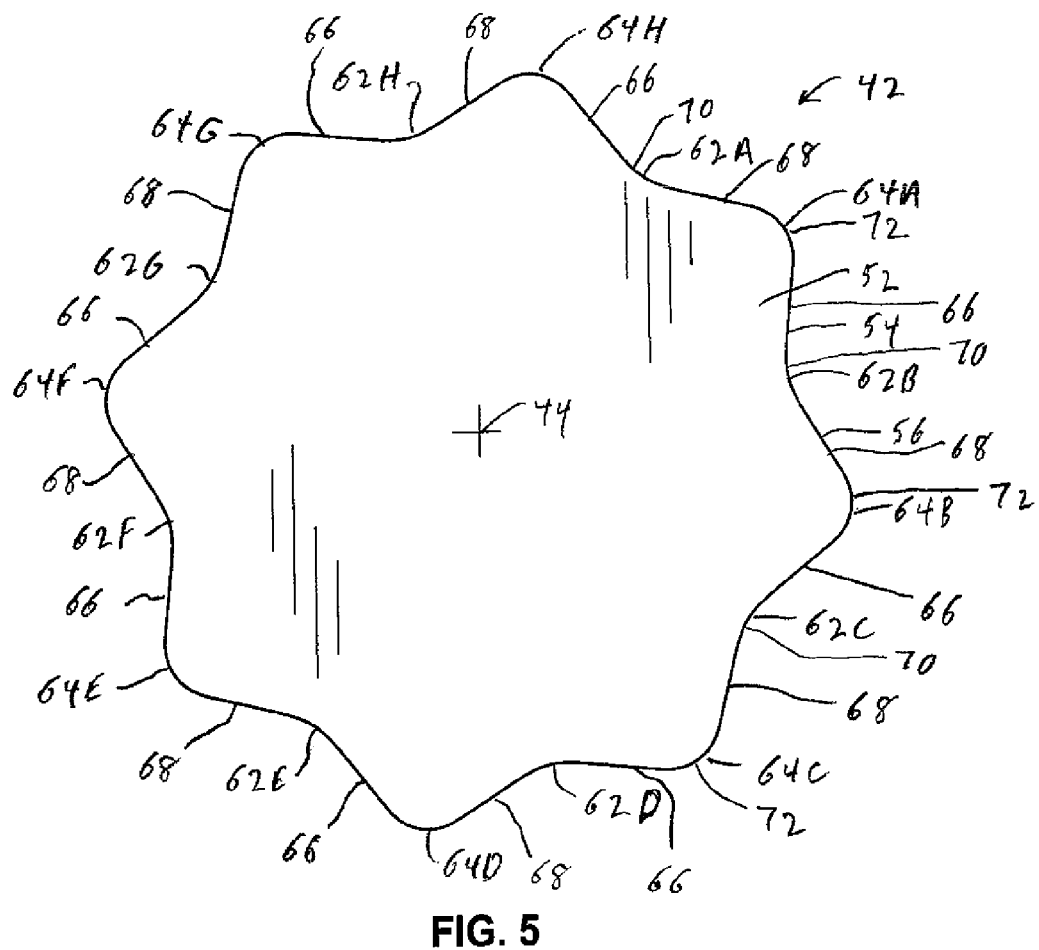
FIG. 5 is a top plan view of the lifting cap of FIG. 4.
Figure 6:
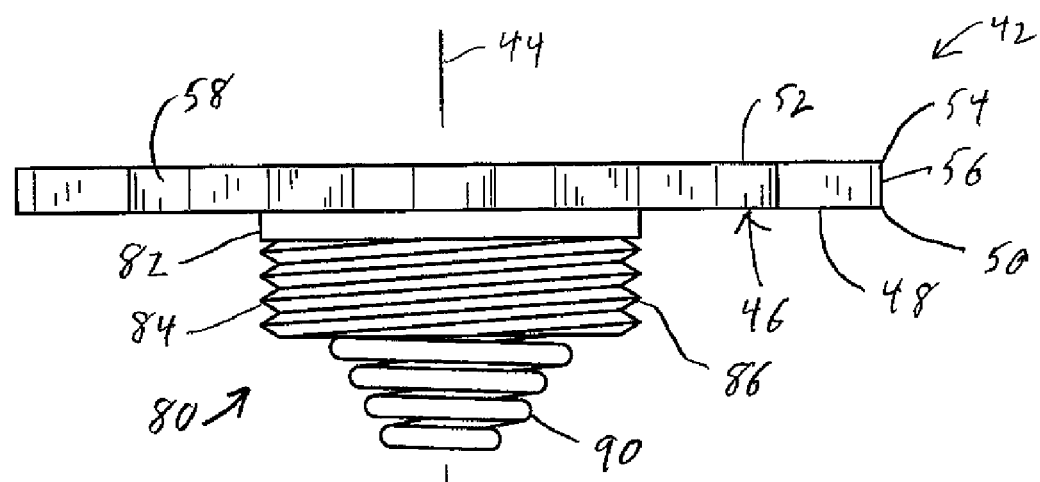
FIG. 6 is a side elevational view of the lifting cap of FIG. 4.
Figure 11:
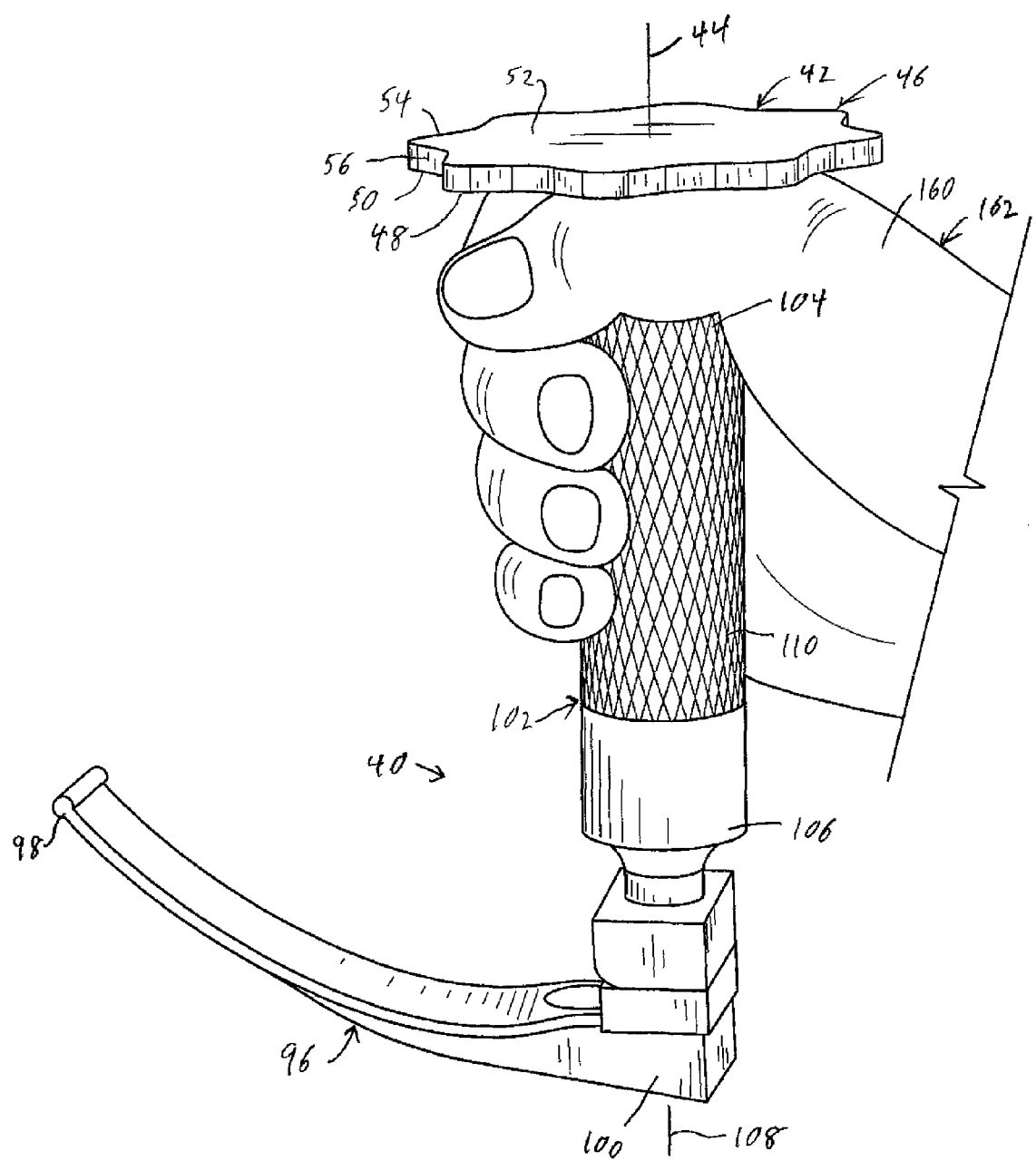
FIG. 11 is a diagrammatic view showing a laryngoscope with the lifting cap of the present disclosure wherein the handle of the laryngoscope is grasped with a right hand of a first user, with the right hand of the first user in abutment with the proximal surface of the abutment member.

A laryngoscope 40 including a lifting cap 42 of the present disclosure is shown in FIG. 11. Lifting cap 42, as shown in FIGS. 4-6, includes a generally linear central axis 44. Lifting cap 42 includes an abutment member 46 such as a generally planar plate. Abutment member 46 includes a generally planar proximal surface 48 having an undulating peripheral edge 50 that extends generally concentrically around central axis 44. Abutment member 46 also includes a generally planar distal surface 52 having an undulating peripheral edge 54 that extends generally concentrically around central axis 44. Distal surface 52 is spaced apart from and generally parallel to proximal surface 48. Distal surface 52 overlies proximal surface 48. Proximal surface 48 and distal surface 52 are both generally perpendicular to axis 44.

Abutment member 46 also includes an undulating peripheral side wall 56 that extends generally linearly between peripheral edge 50 of proximal surface 48 and peripheral edge 54 of distal surface 52, and that extends generally concentrically around central axis 44 and along edges 50 and 54 in an undulating manner. Peripheral edge 50 of proximal surface 48, peripheral edge 54 of distal surface 52, and side wall 56 all extend generally concentrically about central axis 44 in the same non-circular wave-like undulating manner in correspondence with one another, and therefore have the same general configuration. Side wall 56 has an outer surface 58 that is generally smooth. Surface 58 could be roughened or could include a plurality of closely spaced small ribs for enhancing gripping of side wall 56 of lifting cap 42, however, such surface treatments create small pockets or valleys that trap debris and bacteria and that would make it difficult to thoroughly sterilize lifting cap 42. It is therefore preferred that surface 58 of side wall 56 be smooth, although side wall 56 extends in an undulating non-circular manner about axis 44.

As shown in FIG. 5, peripheral edge 50, peripheral edge 54 and peripheral side wall 56 extend around central axis 44 in a generally uniform wave-like undulating manner. Side wall 56 and peripheral edges 50 and 54 form a plurality of finger-grip notches 62A-H and a plurality of peaks 64A-H that are generally uniformly located around central axis 44. Each finger-grip notch 62A-H is located between an adjacent pair of peaks 64A-H. Abutment member 46 as shown in FIGS. 4-6 includes eight finger-grip notches 62A-H and eight peaks 64A-H, but may include fewer or additional finger-grip notches and peaks. Preferably, abutment member 46 has at least five finger-grip notches and five peaks. Each finger-grip notch 62A-H is configured to have a sufficient width between adjacent peaks 64A-H, and a sufficient depth with respect to the outer tip of each adjacent peak 64A-H, to receive a finger of a hand of a user of the laryngoscope 40 and, specifically, the lifting cap 42. As used herein, the term "finger" refers to each of the five digits of a hand, including the digit commonly referred to as a thumb.

Each finger-grip notch 62A-H is foamed by a first generally linear portion 66 of side wall 56, a second generally linear portion 68 of side wall 56, and a concavely curved portion 70 of side wall 56 that connects a proximal end of first linear portion 66 to a proximal end of second linear portion 68. First generally linear portion 66 and second generally linear portion 68 of side wall 56 that form a finger-grip notch 62A-H are disposed at an obtuse angle with respect to one another, and are disposed at an angle between approximately 130 degrees and approximately 145 degrees with respect to one another. Each peak 64A-H includes a convexly curved tip 72. Tip 72 is formed as a portion of side wall 56 and extends from a distal end of a second linear portion 68 of a first finger-grip notch 62A-H to a distal end of a first linear portion 66 of an adjacent second finger grip notch 62A-H. As shown in FIG. 5, side wall 56 and peripheral edges 50 (not shown) and 54 have a generally gear-shaped configuration.

Each finger-grip notch 62A-H is configured to receive a respective finger of a hand of a user and is configured to prevent the finger from slipping along side wall 56 from a position located adjacent concavely curved portion 70 toward tip 72 of an adjacent peak 64A-H. The presence of fluid, such as water or bodily fluids such as blood, saliva or vomit, can make surface 58 of side wall 56 and the proximal and distal surfaces 48 and 52 slippery, such that side wall 56 would be difficult to securely grip with the fingers of a user if the side wall 56 was circular as in lifting cap 22 of FIGS. 2-3. The large finger grip notches 62A-H enable a user to firmly and securely grip side wall 56 and lifting cap 42, even in the presence of fluids, by placing each finger of the hand of the user in a respective finger-grip notch 62A-H, with the thumb of the user generally opposing the remaining four fingers of the hand of the user, and with the palm of the hand of the user located generally adjacent or spaced apart from distal surface 52.

As shown in FIG. 5, each peak 64A-H diametrically opposes another peak 64A-H with respect to axis 44. For example, peak 64A is diametrically opposed to peak 64E. Similarly, each finger-grip notch 62A-H is diametrically opposed to another finger-grip notch 62A-H with respect to central axis 44. For example, finger-grip notch 62A is diametrically opposed to finger-grip notch 62E. Abutment member 46 may have an outer diameter, from a first peak 64A-H to a diametrically opposing peak 64A-H, of approximately three inches. Abutment member 46 may have an inner diameter, from a concavely curved portion 70 of a first finger-grip notch 62A-H to a concavely curved portion 70 of a second diametrically opposed finger-grip notch 62A-H, of approximately two and one-half inches such that each finger-grip notch 62A-H has a depth of approximately one-quarter inch. Abutment member 46 may have a thickness of approximately one-eighth (⅛) inch between proximal surface 48 and distal surface 52.

First linear portion 66 of a first finger-grip notch 62A-H that adjoins a peak 64A-H may be located at approximately a right angle, plus or minus approximately ten to fifteen degrees, to a second linear portion 68 of an adjacent second finger-grip notch 62A-H that adjoins the same peak 64A-H. For example, first linear portion 66 of finger-grip notch 62A that adjoins peak 64H may be located at approximately a right angle, plus or minus approximately ten to fifteen degrees, to a second linear portion 68 of finger-grip notch 62H that also adjoins peak 64H. In addition, a first linear portion 66 of a first finger-grip notch 62A-H may be located generally parallel to, or at a slight angle with respect to, a second linear portion 68 of an adjacent second finger-grip notch 62A-H. For example, first linear portion 66 of finger-grip notch 62H may be located generally parallel to or at a slight angle with respect to second linear portion 68 of finger-grip notch 62A.

Lifting cap 42 also includes a fastener 80 such as an end cap that may be formed substantially identical to end cap 16. Fastener 80 is attached to proximal surface 48 of abutment member 46 generally concentrically with central axis 44. Fastener 80 includes an end wall 82 that is attached to proximal surface 48, and a generally cylindrical wall 84 that extends outwardly from end wall 82 and proximal surface 48 generally perpendicular to proximal surface 48 and concentrically about and along central axis 44. Cylindrical wall 84 includes one or more external threads 86. Cylindrical wall 84 includes a chamber 88 configured to receive a resilient biasing member 90 such as a generally conical spring. Proximal surface 48 of abutment member 46 preferably extends at least approximately seven-eighths (⅞) of an inch radially outwardly from cylindrical wall 84 to peaks 64A-H. Abutment member 46 and fastener 80 may be formed from a metallic material, such as stainless steel, to facilitate sterilization.

As shown in FIG. 11, laryngoscope 40 includes a blade 96 having a first end 98 and a second end 100. First end 98 is adapted to be inserted into the oral opening or mouth of a patient. Laryngoscope 40 also includes a cylindrical handle 102 having a distal first end 104 and a proximal second end 106. Handle 102 includes a generally linear central axis 108 that extends from first end 104 to second end 106. Handle 102 includes a generally tubular shaft having an outer cylindrical peripheral surface 110 that extends generally concentrically about axis 108.

Handle 102 includes a bore that is open at first end 104 such that one or more batteries can be inserted into handle 102 through first end 104. First end 104 of handle 102 is internally threaded, but may alternatively include external threads. Cylindrical wall 84 of fastener 80 is configured to threadably engage first end 104 of handle 102 such that lifting cap 42 is removably attached to first end 104 of handle 102 with central axis 44 of lifting cap 42 located generally parallel to and generally coaxially aligned with central axis 108 of handle 102.

Figure 7:
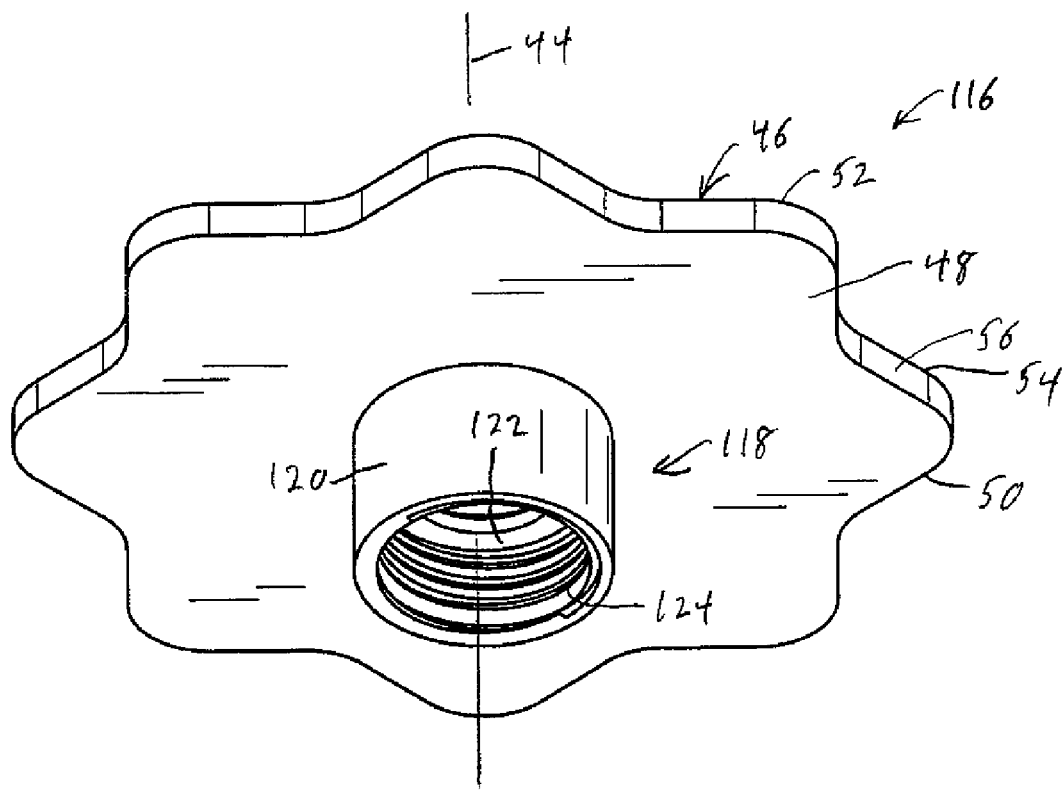
FIG. 7 is a perspective view of a modified embodiment of the lifting cap of the present disclosure including a fastener with internal threads.

Another embodiment of the lifting cap of the present disclosure is shown in FIG. 7 and is identified with reference number 116. Elements of lifting cap 116 that are similar to elements of lifting cap 42 are identified with the same reference number. Lifting cap 116 includes a central axis 44 and an abutment member 46 as included in lifting cap 42. Lifting cap 116 includes a fastener 118 attached to proximal surface 48 of abutment member 46 that is located concentrically with axis 44. Fastener 118 includes a generally cylindrical wall 120 forming an internal chamber 122. Cylindrical wall 120 includes one or more internal threads 124 formed on an internal surface of cylindrical wall 120. Chamber 122 is adapted to receive a biasing member 90. Abutment member 46 and fastener 118 of lifting cap 116 are preferably made from a metallic material, such as stainless steel, to facilitate sterilization. Lifting cap 116 is intended for use with a laryngoscope having a handle wherein the distal end of the handle includes external threads.

Figure 8:
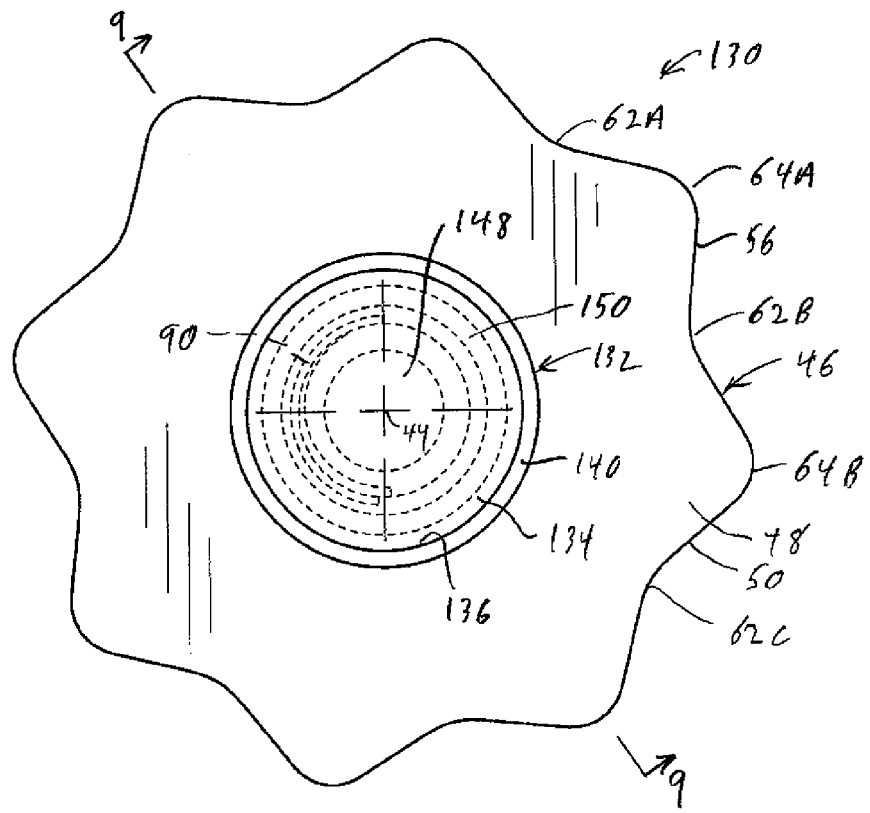
FIG. 8 is a bottom view of a further modified embodiment of the lifting cap of the present disclosure shown with an abutment member and an annular collar formed from a non-metallic material and a fastener located within the collar formed from a metallic material.
Figure 9:
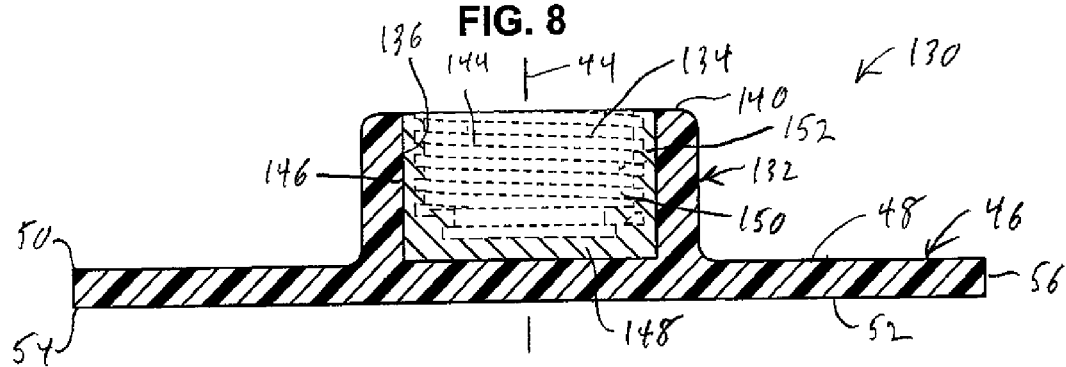
FIG. 9 is a cross sectional view taken along line 9-9 of FIG. 8.
Figure 10:
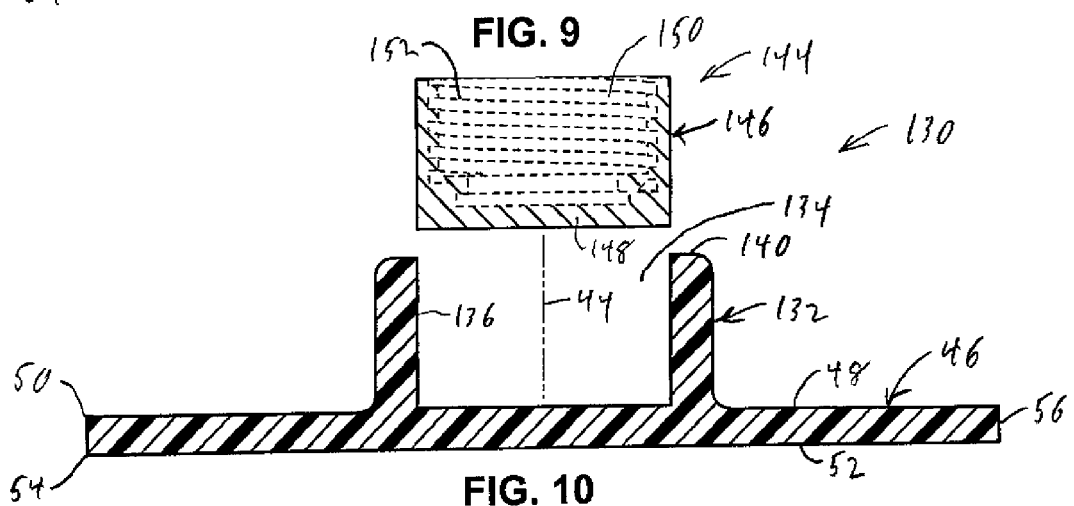
FIG. 10 is an exploded cross sectional view of the lifting cap of FIG. 8.

A further embodiment of a lifting cap of the present disclosure is shown in FIGS. 8-10 and is identified with the reference number 130. The elements of lifting cap 130 that are substantially similar to the elements of lifting cap 42 are identified with the same reference number. Lifting cap 130 includes a generally linear central axis 44 and an abutment member 46 formed in the same manner as the abutment member of lifting cap 42. A generally annular collar 132 is attached to proximal surface 48 of abutment member 46 and extends outwardly therefrom generally concentrically about axis 44. Collar 132 includes an internal chamber 134 formed by a generally cylindrical wall 136. Collar 132 includes a generally circular and annular end wall 140 that is generally parallel to proximal surface 48. Abutment member 46 and collar 132 are preferably integrally formed and attached to one another. Abutment member 46 and collar 132 are preferably made from a non-metallic material, such as plastic. The plastic may be polycarbonate.

Lifting cap 130 also includes a fastener 144 having a generally cylindrical side wall 146 and a bottom wall 148. Fastener 144 includes a chamber 150 formed within side wall 146. An internal surface of side wall 146 includes one or more internal threads 152. Fastener 144 is located within chamber 134 of collar 132 such that bottom wall 148 engages abutment member 46 and such that cylindrical wall 136 of collar 132 extends around and in engagement with side wall 146 of fastener 144. Fastener 144 is preferably made from a metallic material, such as stainless steel. The outer cylindrical surface of the side wall 146 of fastener 144 may be roughened to facilitate attachment between side wall 146 of fastener 144 and cylindrical wall 136 of collar 132. Fastener 144 is attached to collar 132 and thereby to proximal surface 48 of abutment member 46. Fastener 144 is generally concentrically located about axis 44. Lifting cap 130 is configured to be removably attached to a distal end of the handle of a laryngoscope having external threads. Lifting cap 130 is lighter in weight than similar sized lifting caps 42 and 116.

Figure 12:
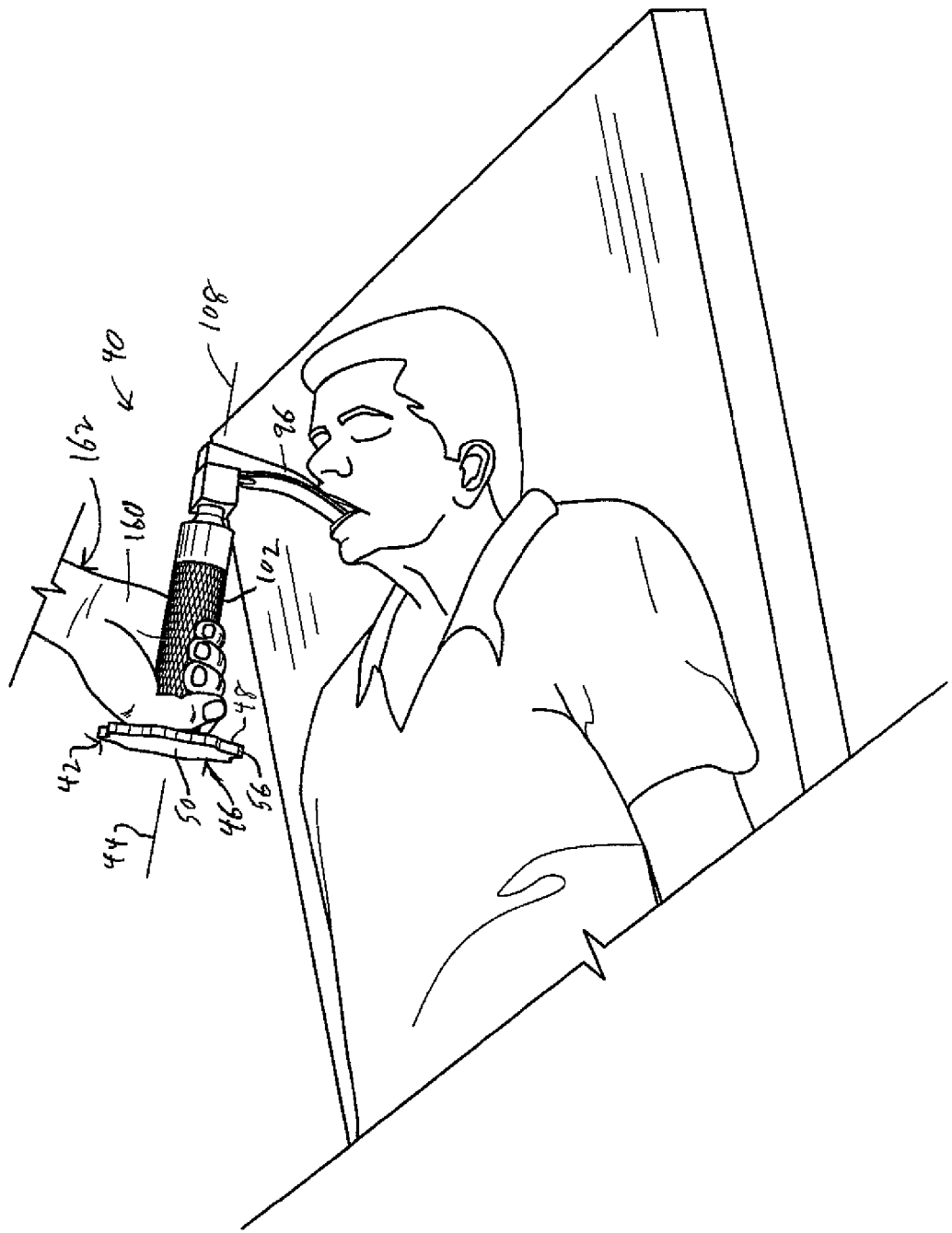
FIG. 12 is a diagrammatic view showing the tip of the blade of the laryngoscope inserted into the mouth of a patient with the right hand of the first user grasping the handle of the laryngoscope and in abutting engagement with the abutment member of the lifting cap.
Figure 13:
FIG. 13 is a diagrammatic view showing the left hand of a second user grasping the peripheral side wall of the abutment member with the fingers of the left hand of the second user located in the finger-grip notches of the abutment member while the right hand of the first user is being released from the handle of the laryngoscope.

As shown in FIGS. 1 and 2, prior art laryngoscopes were gripped with the left hand of a single user for insertion into the oral opening of a patient. As shown in FIGS. 11-13, laryngoscope 40 with lifting cap 42 of the present disclosure is initially gripped with a right hand 160 of a first user 162, with right hand 160 abutting proximal surface 48 of abutment member 46. As shown in FIG. 12, first user 162 then inserts first end 98 of blade 96 into the oral opening of the patient.

While first user 162 is inserting blade 96 into the oral opening of the patient with right hand 160, the left hand of first user 162 may be used to perform external manipulation of the vocal chords of the patient by appropriately contacting the external surface of the throat of the patient with the left hand of first user 162 to avoid damaging the vocal chords of the patient during the intubation procedure. The first user therefore does not need to apply a lifting force to laryngoscope 40 parallel to axes 108 and 44. When blade 96 of laryngoscope 40 is located in the desired position with respect to the patient, as shown in FIG. 13, side wall 56 of abutment member 46 can be grasped by a hand 164, either a right hand or a left hand, of a second user 166. The fingers of hand 164 are positioned in respective finger-grip notches 62A-H of abutment member 46 such that hand 164 of second user 166 can firmly and securely grip abutment member 46 while right hand 160 of first user 162 grips handle 102 of laryngoscope 40.

After hand 164 of second user 166 grips abutment member 46, right hand 160 of first user 162 can be released from laryngoscope 40, while second user 166 maintains laryngoscope 40 in the desired position. Right hand 160 of first user 162 can then be used to insert an endotracheal tube into the oral opening and larynx of the patient, while the left hand of first user 162 performs external manipulation of the vocal chords of the patient to avoid damage to the vocal chords of the patient. When the endotracheal tube is properly inserted into the patient, first user 162 may again grip handle 102 with right hand 160, or with the left hand of first user 162, whereupon second user 166 releases hand 164 from abutment member 46. First user 162 can then remove blade 96 from the oral opening of the patient. A laryngoscope including lifting caps 116 or 130 may be used in the same manner. A laryngoscope including lifting caps 42, 116 or 130 may also be used by a single user if desired.

Various features of the invention have been particularly shown and described in connection with the illustrated embodiments of the invention, however, it must be understood that these particular arrangements merely illustrate, and that the invention is to be given its fullest interpretation within the terms of the appended claims.

The invention claimed is:

1. A method of performing oral endotracheal intubation with a laryngoscope, the method comprising the steps of:
grasping a handle of the laryngoscope with a right hand of a first user, the laryngoscope including a curved blade attached to a second end of the handle and an abutment member attached to a first end of the handle, the abutment member including a proximal surface having an undulating peripheral edge, a distal surface having an undulating peripheral edge, and an undulating peripheral side wall extending generally linearly between the peripheral edge of the proximal surface and the peripheral edge of the distal surface, the side wall forming a plurality of finger-grip notches disposed about a central axis of the abutment member;

inserting the curved blade into an oral opening of a patient, while the right hand of the first user is grasping the handle;

maneuvering the curved blade while in the oral opening of the patient to thereby establish a desired position of the laryngoscope, while the right hand of the first user is grasping the handle;

externally manipulating vocal chords of the patient with a left hand of the first user, while the right hand of the first user is grasping the handle and performing the maneuvering step;

grasping the side wall of the abutment member with a hand of a second user by placing fingers of the hand of the second user in the respective finger-grip notches of the abutment member to thereby maintain the laryngoscope in the desired position established by the right hand of the first user during the maneuvering step, while the right hand of the first user is grasping the handle;

releasing the right hand of the first user from the handle subsequent to the maintaining of the laryngoscope in the desired position via the grasping of the side wall of the abutment member with the hand of the second user;

externally manipulating the vocal chords of the patient with the left hand of the first user, while inserting an endotracheal tube into the oral opening of the patient with the right hand of the first user, and while the hand of the second user is maintaining the laryngoscope in the desired position via the grasping of the side wall of the abutment member;

grasping the handle with the right hand or the left hand of the first user subsequent to the insertion of the endotracheal tube into the oral opening of the patient and while the hand of the second user is maintaining the laryngoscope in the desired position via the grasping of the side wall of the abutment member;

releasing the hand of the second user from the side wall of the abutment member subsequent the grasping of the handle with the right hand or the left hand of the first user; and removing the curved blade from the oral opening of the patient with the right hand or the left hand of the first user, subsequent the releasing of the hand of the second user from the side wall of the abutment member.

2. The method of claim 1 including abutting the first right hand of the first user against the proximal surface of the abutment member when the first user grasps the handle with the right hand of the first user.

3. The method of claim 1, wherein the grasping of the handle with the right hand or the left hand of the first user is performed using only the left hand of the first user, and wherein the removing of the curved blade from the oral opening of the patient with the right hand or the left hand of the first user is performed using only the left hand of the first user.

* * * * *